United States Patent [19]

Matusch et al.

[11] Patent Number: 5,519,018

[45] Date of Patent: May 21, 1996

[54] SUBSTITUTED PHENOLS AND THEIR USE FOR THE TREATMENT OF DISORDERS CAUSED BY CELL PROLIFERATION

[75] Inventors: Rudolf Matusch; Manfred Hunz; Jörg Czech; Hans-Harald Sedlacek, all of Marburg, Germany

[73] Assignee: Behringwerke Aktiengesellschaft, Marburg, Germany

[21] Appl. No.: 431,794

[22] Filed: May 1, 1995

Related U.S. Application Data

[63] Continuation of Ser. No. 117,759, Sep. 8, 1993, abandoned.

[30] Foreign Application Priority Data

Sep. 10, 1992 [DE] Germany .................. 42 30 262.5

[51] Int. Cl.⁶ .................. A61K 31/41; A61K 31/535; C07D 295/30
[52] U.S. Cl. .................. 514/218; 514/239.5; 514/255; 514/329; 514/400; 514/567; 514/641; 540/605; 544/164; 544/382; 546/223; 560/39; 564/251; 564/274
[58] Field of Search .................. 514/567, 641, 514/400, 239.5, 329, 255, 218; 544/164, 382; 540/605; 546/223; 548/336.1; 560/39; 562/478; 564/251, 274

[56] References Cited

U.S. PATENT DOCUMENTS

| 4,828,568 | 8/1989 | Konrad et al. .................. 564/274 X |
| 4,833,164 | 5/1989 | Batt .................. 514/647 |

FOREIGN PATENT DOCUMENTS

| 0183532A2 | 5/1986 | European Pat. Off. . |
| 0238868A2 | 9/1987 | European Pat. Off. . |
| 0322738A2 | 7/1989 | European Pat. Off. . |

OTHER PUBLICATIONS

Ulbricht et al., Preparation of New Azomethines and their Derivatives as Antiinflammatory Agents, 110(21) :192427d (May 1989).

Cushman et al., Synthesis and Evaluation of New Protein-Tyrosine Kinase Inhibitors. Part 2. Phenylhydrazones., Bioorganic & Medicinal Chemistry Letters, 1(4):215–218 (1991).

J. March, "Advanced Organic Chemistry," pp. 1084–1085. (1976).

H. Beyer, "Lehrbuch der Organischen Chemie," p.481 (1984).

Mattar et al., "Inhibition of the Epidermal Growth Factor Receptor Tyrosine Kinase Activity by Leflunomide," FEBS Letters, 334(2): 161–164 (1993).

Yoneda et al., "The Antiproliferative Effects of Tyrosine Kinase Inhibitors Tyrphostins on a Human Squamous Cell Carcinoma" in Vitro and in Nude Mice, Cancer Research, 51:4430–4435 (1991).

*Primary Examiner*—Jacqueline Haley
*Attorney, Agent, or Firm*—Finnegan, Henderson, Farabow, Garrett & Dunner

[57] ABSTRACT

Substituted phenols of the formula I

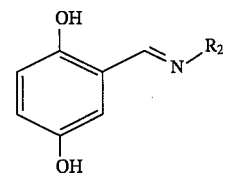

processes for their preparation and compositions containing substituted phenols of the formulae I and II

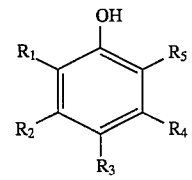

for the treatment of disorders caused by cell proliferation, such as psoriasis, tumor disorders and immunological disorders, are described.

11 Claims, No Drawings

SUBSTITUTED PHENOLS AND THEIR USE FOR THE TREATMENT OF DISORDERS CAUSED BY CELL PROLIFERATION

This application is a continuation Ser. No. 08/117,759 filed Sept. 8, 1993, now abandoned.

The invention relates to substituted phenols of the formula I, processes for their preparation and compositions containing substituted phenols of the formulae I and II for the treatment of disorders caused by cell proliferation, such as psoriasis, tumor disorders and immunological disorders.

It is already known that substituted phenols are suitable for the treatment of tumor disorders (EP 0322738 and EP 0238868), whereby it has been found that certain substituted phenols inhibit tyrosine kinase activity of the EGF (epidermal growth factor) receptor and thus block the growth of tumor cells. It is further known that tyrosine kinase play a crucial part in the T- and B-cell activation of the immune system and in the activation of mast cells and basophilic leucocytes and thus the secretion of histamine.

It is an object of the invention to obtain better compounds for the treatment of tumor disorders and immunological disorders.

It has surprisingly been found that substituted phenols of the formulae I and II have an activity against proliferating tumor cells, in which they strongly inhibit the EGF receptor tyrosine kinase.

The invention relates to compounds of the formula I

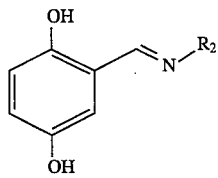

where $R_2$ is methyl, ethyl, hexyl, isopropyl, N-dimethylamino, N-morpholino, benzyl, N-piperidine, N-homopiperidine, 4-benzoic acid, 3-halophenyl, 4-halophenyl, N-piperazine, N-4-methylpiperazine, or an amino acid residue with the exception of glycine and methionine, preferably

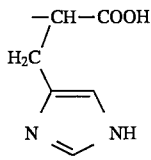

or its esters.

The invention also relates to a process for the preparation of the compounds of the formula I, which comprises dissolving or suspending 2,5-dihydroxybenzaldehyde in a suitable solvent, preferably toluene, and heating with the equivalent amount of the corresponding amine under reflux in a water-separating apparatus until the elimination of water is complete, or dissolving 2,5-dihydroxy-benzaldehyde with the equimolar amount of the corresponding amine in dried methanol and heating to about 60° C., preferably for about 24 h. After cooling, the solvent is stripped off, for example in a rotary evaporator under reduced pressure. The residue is taken up in toluene/ethanol and recrystallized.

The invention additionally relates to pharmaceuticals which contain a compound of the formula I or a compound of the formula

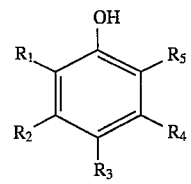

where $R_1$ and $R_2$ are H or together are a fused aromatic system, preferably a carbocyclic system preferably having up to 8 carbon atoms, which can be substituted, preferably by up to 2 hydroxy groups $R_3$ is H or OH $R_4$ and $R_5$ independently of one another are H, $C_1$–$C_4$-alkyl, preferably methyl, sulfonic acid, aryl, preferably phenyl, hydroxyl, CHO or halogen, where at least one of the radicals $R_1$–$R_5$ is not H or a Schiff's base of the formula —CH=N—$R_6$, and $R_6$ is alkyl, N-dimethylamino, cyclohexyl, N-morpholino, benzyl, N-piperidine, N-homopiperidine, aryl, haloaryl, carboxyaryl or hydroxyaryl where aryl is preferably phenyl, or is N-piperazine, N-4-methylpiperazine or an amino acid radical, preferably

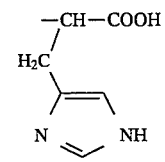

or its esters.

For $R_3$=OH the invention also relates to the corresponding quinones.

These pharmaceuticals contain substituted phenols according to the invention. The pharmaceuticals according to the invention are prepared by bringing at least one substituted phenol into a suitable administration form, if appropriate using further auxiliaries and/or excipients. The auxiliaries and excipients are derived from the group comprising excipients, preservatives and other customary auxiliaries.

For the control of tumor disorders and immune diseases, the compounds according to the invention can be administered in various ways, for example, they can be administered intravenously, intramuscularly, intraperitoneally, subcutaneously, as a continuous drip infusion, rectally or orally. In the case of acute disease conditions, administration as a continuous drip infusion is to be preferred. For continuous medication, for example, oral administration is indicated.

For example, for oral administration forms auxiliaries such as starches, e.g. potato, corn or wheat starch, cellulose or its derivatives, in particular microcrystalline cellulose, silica, various sugars such as lactose, magnesium carbonate and/or calcium phosphates can be used. It is furthermore advantageous to add auxiliaries which improve the tolerability of the medicaments to the oral administration forms, such as for example, mucilaginous agents and resins. To improve tolerability, the medicaments can also be administered in the form of enteric-coated capsules. Moreover, it may be advantageous to add a sustained-release agent to the administration form, or to a component of the combination preparation, if appropriate in the form of permeable membranes, such as for example, those based on cellulose or polystyrene, or ion exchangers.

The dose of the pharmaceuticals according to the invention to be used is dependent on various factors such as the administration form of the medicament and the condition, weight and nature of the disorder of the patient. A daily dose of about 5000 mg of a substituted phenol should only be exceeded for a short time, however. About 10 to 2500 mg of substituted phenol are preferred as a daily dose for a human of body weight about 70 kg. The daily dose of the substituted phenols can be administered in the form of an individual administration or in several smaller doses. Administration in 3 to 8 doses per day is preferred. In some cases, a continuous supply of the substituted phenols may be indicated, e.g. in the form of a continuous drip infusion.

These pharmaceuticals are suitable for the control of diseases which are caused by uncontrolled cell proliferation (cell activation). They are effective for the inhibition of cell proliferation, in particular of immune cell and tumor cell proliferation, and the inhibition of the activation of mast cells and basophilic leucocytes, i.e. for the treatment of psoriasis, tumor disorders and immune diseases.

EXAMPLES

Example 1–14

General working procedure for the preparation of N-substituted 2,5-dihydroxybenzaldimines (method A)

250 mg (1.8 mmol) of 2,5-dihydroxybenzaldehyde are dissolved or suspended in toluene using the equimolar amount of the corresponding amine and the mixture is heated under reflux for 12 h in a water-separating apparatus. After cooling, the solvent is stripped off under reduced pressure in a rotary evaporator. The residue is taken up in toluene/ethanol and recrystallized.

General working procedure for the preparation of N-substituted 2,5-dihydroxybenzaldimines (method B)

250 mg (1.8 mmol) of 2,5-dihydroxybenzaldehyde are dissolved in dried methanol with the equimolar amount of the corresponding amine and the solution is heated at 60° C. for 24 h. After cooling, the solvent is stripped off under reduced pressure in a rotary evaporator. The residue is taken up in toluene/ethanol and recrystallized.

|  | Amine | Method | M.p. (°C.) | Yield (% of theory) |
|---|---|---|---|---|
| 1. 4-[N-(2',5'-Dihydroxybenzylidene)amino]-benzoic acid | 4-Aminobenzoic acid | A | 205 | 78 |
| 2. 2,5-Dihydroxy-N-methylbenzaldimine | Methylamine | B | 122 | 65 |
| 3. N-Benzyl-2,5-dihydroxybenzaldimine | Benzylamine | A | 118 | 40 |
| 4. 2,5-Dihydroxy-N,N-dimethylbenzaldehyde hydrazone | N,N-dimethylhydrazine | B | 111 | 25 |
| 5. (S)-α-N-(2,5-Dihydroxybenzylidene)histidine methyl ester | Histidine methyl ester | B | 110 | 15 |
| 6. N-Hexyl-2,5-dihydroxybenzaldimine | Hexylamine | A | 95 | 75 |
| 7. N-Ethyl-2,5-hydroxybenzaldimine | Ethylamine | B | 145 | 75 |
| 8. 2,5-Dihydroxy-N-isopropylbenzaldimine | Isopropylamine | B | 135 | 70 |
| 9. N-(4'-Chlorophenyl)-2,5-dihydroxybenzaldimine | 1-Amino-4-chlorobenzene | A | 170 | 70 |
| 10. 2,5-Dihydroxy-N-piperidinobenzaldimine | 1-Aminopiperidine | B | 177 | 50 |
| 11. 2,5-Dihydroxy-N-morpholinobenzaldimine | 4-Aminomorpholine | B | 172 | 60 |
| 12. 2,5-Dihydroxy-N-(4'-methylpiperazino)benzaldimine | 1-Amino-4-methylpiperazine | B | 250 | 65 |
| 13. (S)-N-(2',5'-Dihydroxybenzylidene)tyrosine methyl ester | Tyrosine | B | 131 | 20 |
| 14. (S)-N-(2',5'-Dihydroxybenzylidene)phenylalanine methyl ester | Phenylalanine | B | 107 | 20 |

Example 15

Test for EGF receptor tyrosine kinase inhibition

The starting material for tyrosine kinase activity was the human tumor cell line A 431 (ATCC CRL 1555), which was cultured in RPMI 1640 medium+10% FCS. This cell line expresses a large number of EGF receptors which have tyrosine kinase activity on the cell surface. The cells were cultured almost to confluence, washed with PBS (phosphate buffered saline, pH 7.2), scraped off the culture flask and incubated at 4° C. for 1 h, subjected to 20 strokes in a Potter and centrifuged at 1000 g for 30'. The supernatant was centrifuged at 20000 g for a further 20 min and the pellet was taken up in 100 µl per 1×10$^6$ cells as the membrane preparation.

The tyrosine kinase activity of the EGF receptor (EGFRTK) was measured using poly(Glu, Ala, Tyr), 6:3:1, as the substrate. The cell membranes were pretreated with 1000 nM EGF at RT for 15' and then added to the batch which contains the inhibitor, substrate (3 mg/ml), $Mg^{2+}$/$Mn_{2+}$ (8 mM/1.6 mM), 0.16% Triton X-100 and sodium orthovanadate (20 µM) in 100 mM HEPES (N-2-hydroxyethylpiperazine-N' -2-ethanesulfonic acid), pH 7.5, preincubated and the reaction initiated by addition of gamma-$^{32}$P ATP (32 µM). After 15' at 30° C., the substrate was precipitated with 10% TCA (trichloroacetic acid), filtered on a milliliter filtration plate (Millipore Corporation, Massachusetts, USA), washed and dried. The incorporation of $^{32}$P was determined by means of a liquid scintillation counter.

Results:

The substituted phenols were tested at a maximum concentration of 51 µg/ml and diluted stepwise 1:10. $IC_{50}$ indicates the concentration at which 50% of the starting enzyme activity was inhibited (Table 1).

Example 16

Test for 3',5'-cAMP-dependent protein kinase inhibition

The catalytic subunit of the cAMP-dependent protein kinase (PKA) (Sigma) was reconstituted as described by Sigma (Sigma Chemical Co., St. Louis, Mo. USA). The enzyme activity was measured using Kemptide (Sigma)

(Leu-Arg-Arg-Ala-Ser-Leu-Gly) as a substrate. The inhibitor was preincubated with enzyme, substrate (190 μM), $Mg^{2+}$ (5 mM), 0.25 mg/ml of BSA and 3.75 mM mercaptoethanol in 50 mM MOPS (4-morpholinopropanesulfonic acid), pH 6.9. The reaction was initiated by addition of gamma-$^{32}$P ATP (40 μM) After 15'at 30° C., an aliquot part was added to p81 ion exchanger (2×2 cm; Whatman Paper Ltd., Great Britain), immersed in 75 mM $H_3PO_4$, washed, dried, and the incorporation of $^{32}$P was determined by means of a liquid scintillation counter.

Results:

The substituted phenols were tested at a maximum concentration of 40 μ g/ml, and the % inhibition indicates the inhibition of the starting enzyme activity (Table 1).

TABLE 1

Inhibition of the enzymatic activity of protein kinases by substituted phenols.

| Substance | EGFRTK $IC_{50}$, μg/ml | PKA % inhib. at 40 μg/ml |
|---|---|---|
| Hydroquinone | 0.1 | n.t. |
| Benzoquinone | 0.05 | 45 |
| Menadiol | 26.2 | 0 |
| Naphthoquinone | 0.2 | 46 |
| 2-Methylhydroquinone | 1.1 | 46 |
| Potassium hydroquinone-2-sulfonate | 1.84 | 1 |
| 2-Phenylhydroquinone | 1.03 | 25 |
| 2-tert-Butylhydroquinone | 0.95 | 22 |
| Pyrocatechol | 1.6 | 0 |
| Gentisaldehyde | 20–30 | n.t. |
| 1,2,4-Trihydroxybenzene | 24.0 | 0 |
| 1,4-Naphthodiol | 1.5 | 76 |
| 1,4-Anthraquinone | 0.58 | n.t. |
| 2,5-Dihydroxy-N-(4'-hydroxyphenyl)-benzaldimine | 12.63 | n.t. |
| 2,5-Dihydroxy-N-phenylbenzaldimine | 19.04 | n.t. |
| 3-[-(2',5'-Dihydroxybenzylidene)-amino]benzoic acid | 20.05 | 0 |
| 4-[N-(2',5'-Dihydroxybenzylidene)-amino]benzoic acid (Ex. 1) | 17.37 | 0 |
| 5-[N-(2',5'-Dihydroxybenzylidene)-amino]-2-hydroxybenzoic acid | 7.45 | 0 |
| N-Hexyl-2,5-dihydroxybenzaldimine (Ex. 6) | 21.16 | 0 |
| 2,5-Dihydroxy-N-methylbenzaldimine (Ex. 2) | 1.98 | 0 |
| 2,5-Dihydroxy-N-isopropylbenzaldimine (Ex. 7) | 12.25 | 0 |
| Quinhydrone | 0.126 | 0 |
| N-Isopropyl-2,5-dihydroxybenzaldimine (Ex. 8) | 8.3 | 0 |
| N-Benzyl-2,5-dihydroxybenzaldimine (Ex. 3) | 1.7 | 0 |
| 2,3-Dimethylhydroquinone | 0.641 | 71 |
| 2-Chlorohydroquinone | 1.89 | 0 |
| 2-Chlorobenzoquinone | 1.38 | 29 |
| 2,5-Dihydroxy-N-piperidinobenzaldimine (Ex. 10) | 10.51 | 0 |
| 2,5-Dihydroxy-N-morpholinobenzaldimine (Ex. 11) | 2.77 | 0 |
| 2,5-Dihydroxy-N-(4'-methylpiperazino)benzaldimine (Ex. 12) | 0.56 | 0 |
| N-Homopiperidino-2,5-dihydroxybenzaldimine | 4.08 | 0 |
| 4-[N-(2',5'-Dihydroxybenzyl)-amino]benzoic acid | 4.61 | 61 |
| N-Cyclohexyl-2,5-dihydroxybenzaldimine | 9.8 | 61 |
| 2,5-Dihydroxy-N,N-dimethylbenzaldehyde hydrazone (Ex. 4) | 1.38 | 63 |
| (S)-alpha-N-(2',5'-Dihydroxybenzylidene)histidine methyl ester (Ex. 5) | 12.64 | 0 |

Example 17

Test for inhibition of EGF- or bFGF-stimulated proliferation of tumor cells $2 \times 10^3$ hela cells per well were inoculated into a 96-well microtiter plate (in RPMI+1% FCS). After 24 h, the medium was changed to RPMI+0.5% FCS and various concentrations of the test substance±EGF (0.1 nM)/bFGF (1 ng/ml) were added. Each group consisted of 4 wells; the control was only incubated±growth factor. After 65 h, 50 μof MTT (2.5 mg/ml in PBS) were added and the supernatant was removed after 7 h. The colored substance formed by the living cells was dissolved by addition of 100 μl of DMSO/well. The absorption was measured at 492 nm for each well with the aid of a 340 CC Multiscan photometer (Flow).

Results:

The mean value is formed from the 4 wells of a group and the absorption difference between the controls± growth factor (A) and between the groups with test substance± growth factor (B) is determined. The % inhibition of the stimulation of growth factor is calculated by $$100 - \frac{B \times 100}{A} \%$$

and is listed in Table 2.

TABLE 2

| Substance | EGF stimulation % inhibition at μg/ml | | | |
|---|---|---|---|---|
| | 0.2 | 1 | 5 | 25 |
| Hydroquinone | | 29 | 43 | |
| Benzoquinone | | 36 | 55 | |
| Menadiol | | n.t. | | |
| Naphthoquinone | | 11 | tox | |
| 2-Methylhydroquinone | | 21 | 66 | |
| Potassium hydroquinone-2-sulfonate | | | 6 | 14 |
| 2-Phenylhydroquinone | | 11 | 66 | |
| 2-tert-Butylhydroquinone | | 21 | 52 | |
| Pyrocatechol | 16 | 35 | | |
| Gentisaldehyde | | 0 | 16 | |
| 1,2,4-Trihydroxybenzene | | 5 | tox | |
| 1,4-Naphthodiol | 29 | tox | | |
| 1,4-Anthraquinone | | 33 | tox | |
| 2,5-Dihydroxybenzylidene-4-hydroxyaniline | | | 39 | tox |
| 2,5-Dihydroxybenzylideneaniline | | | 24 | tox |
| (2,5-Dihydroxybenzylidene)-3-aminobenzoic acid | | | 44 | tox |
| (2,5-Dihydroxybenzylidene)-4-aminobenzoic acid (Ex. 1) | | | 48 | tox |
| (2,5-Dihydroxybenzylidene)-5-amino-2-hydroxybenzoic acid | | | 51 | tox |
| N-Hexyl-2,5-dihydroxybenzaldimine (Ex. 6) | | | 18 | tox |
| N-Methyl-2,5-dihydroxybenzaldimine (Ex. 2) | | | 21 | tox |
| N-Ethyl-2,5-dihydroxybenzaldimine (Ex. 7) | | | 28 | tox |
| Quinhydrone | | 12 | 64 | |
| N-Isopropyl-2,5-dihydroxybenzaldimine (Ex. 8) | | | 28 | tox |
| N-Benzyl-2,5-dihydroxybenzaldimine (Ex. 3) | | | 28 | tox |
| 2,3-Dimethylhydroquinone | | | 17 | tox |
| 2-Chlorohydroquinone | | | 46 | tox |
| 2-Chlorobenzoquinone | | | 29 | tox |
| (2,5-Dihydroxybenzylidene)-1-aminopiperidine (Ex. 10) | | | n.t. | |
| (2,5-Dihydroxybenzylidene)-4-aminomorpholine (Ex. 11) | | | 17 | tox |
| (2,5-Dihydroxybenzylidene)-1-amino-4-methylpiperazine (Ex. 12) | | | 21 | tox |
| (2,5-Dihydroxybenzylidene)-1-aminohomopiperidine | | | tox | |
| N-2,5-Dihydroxybenzyl-4-aminobenzoic acid | | | 36 | tox |
| N-Cyclohexyl-2,5-dihydroxybenzaldimine | | | 39 | 64 |
| N-(2,5-Dihydroxybenzylidene)-N',N'-di- | | | 46 | tox |

TABLE 2-continued

| Substance | EGF stimulation % inhibition at μg/ml | | | |
|---|---|---|---|---|
| | 0.2 | 1 | 5 | 25 |
| methylhydrazine (Ex. 4) (S)-alpha-N-(2',5'-Dihydroxybenzylidene)-histidine methyl ester (Ex. 5) | | | 10 | 44 | n.t. = not tested
tox = toxic

We claim:

1. A compound of the formula I

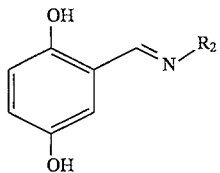

where $R_2$ is methyl, ethyl, hexyl, isopropyl, N-dimethylamino, N-morpholino, benzyl, N-piperidine, N-homopiperidine, 4-benzoic acid, 3-halophenyl, 4-halophenyl, N-piperazine, N-4-methylpiperazine, or an amino acid residue with the exception of glycine and methionine, or its esters.

2. A compound according to claim 1, wherein the amino acid residue is

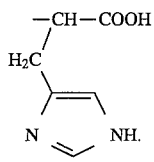

3. A pharmaceutical, which contains a compound of the formula I as claimed in claim 1 or of the formula II

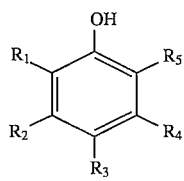

where $R_1$ and $R_2$ are H or together are a carbocyclic system having up to 8 carbon atoms substituted by up to two hydroxyl groups, $R_3$ is H or OH, with the proviso that when $R_1$ and $R_2$ are together a carbocyclic system having 6 carbons, $R_3$ is OH, $R_4$ and $R_5$ independently of one another are H, $C_1$–$C_4$-alkyl, sulfonic acid, aryl, hydroxyl, CHO or halogen or a Schiff's base of the formula —CH=N—$R_6$, where at least one of the radicals $R_1$–$R_5$ is not H, and $R_6$ is alkyl, N-dimethylamino, cyclohexyl, N-morpholino, benzyl, N-piperidine, N-homo-piperidine, aryl, haloaryl, carboxyaryl or hydroxyaryl, or is N-piperazine, N-4-methyl-piperazine or an amino acid radical, or its esters and an auxiliary and/or excipient.

4. A pharmaceutical according to claim 3, wherein $R_4$ and $R_5$ are methyl.

5. A pharmaceutical according to claim 3, wherein $R_4$ and $R_5$ are phenyl.

6. A pharmaceutical according to claim 3, wherein the aryl in $R_6$ is phenyl.

7. A pharmaceutical according to claim 3, wherein $R_1$ and $R_2$ together are a carbocyclic system having up to 8 carbon atoms substituted by up to 2 hydroxyl groups.

8. A method for the treatment of diseases which are caused by uncontrolled proliferation of cells which comprises administering to a host in need thereof an effective amount of a compound of the formula I as claimed in claim 1.

9. A method as claimed in claim 8, where psoriasis is treated.

10. A method for the treatment of diseases which are caused by the uncontrolled proliferation of cells which comprises administering to a host in need thereof an effective amount of a compound of the formula II:

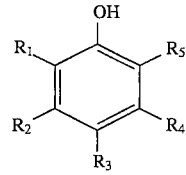

wherein $R_1$ and $R_2$ are H or together are a carbocyclic system having up to 8 carbon atoms substituted by up to two hydroxyl groups, $R_3$ is H or OH, with the proviso that when $R_1$ and $R_2$ are together a carbocyclic system having 6 carbons, $R_3$ is OH, $R_4$ and $R_5$ independently of one another are H, $C_1$–$C_4$-alkyl, sulfonic acid, aryl, hydroxyl, CHO or halogen or a Schiff's base of the formula —CH=N—$R_6$, where at least one of the radicals $R_1$–$R_5$ is not H, and $R_6$ is alkyl, N-dimethylamino, cyclohexyl, N-morpholino, benzyl, N-piperidine, N-homopiperidine, aryl, haloaryl, carboxyaryl or hydroxyaryl, or is N-piperazine, N-4-methyl-piperazine or an amino acid radical, or its ester and an auxiliary and/or excipient.

11. A method as claimed in claim 10, where psoriasis is treated.

* * * * *